US012727861B2

(12) United States Patent
Igarashi

(10) Patent No.: US 12,727,861 B2
(45) Date of Patent: Sep. 8, 2026

(54) ULTRASOUND DIAGNOSTIC APPARATUS AND CONTROL METHOD OF ULTRASOUND DIAGNOSTIC APPARATUS

(71) Applicant: FUJIFILM Corporation, Tokyo (JP)

(72) Inventor: Riki Igarashi, Kanagawa (JP)

(73) Assignee: FUJIFILM Corporation, Tokyo (JP)

( * ) Notice: Subject to any disclaimer, the term of this patent is extended or adjusted under 35 U.S.C. 154(b) by 191 days.

(21) Appl. No.: 18/324,602

(22) Filed: May 26, 2023

(65) Prior Publication Data

US 2023/0380811 A1 Nov. 30, 2023

(30) Foreign Application Priority Data

May 30, 2022 (JP) ................................ 2022-087604

(51) Int. Cl.
*A61B 8/00* (2006.01)

(52) U.S. Cl.
CPC ............ *A61B 8/5207* (2013.01); *A61B 8/461* (2013.01)

(58) Field of Classification Search
CPC .......... A61B 8/4263; A61B 2034/2051; A61B 8/4245; G16H 50/20
See application file for complete search history.

(56) References Cited

U.S. PATENT DOCUMENTS 7,648,460 B2 * 1/2010 Simopoulos ........... G16H 30/20 600/443
2009/0327172 A1 * 12/2009 Liu ........................ G06N 20/00 706/12

(Continued)

FOREIGN PATENT DOCUMENTS

EP 3 445 249 B1 4/2020
JP 2021-29675 A 3/2021

(Continued)

OTHER PUBLICATIONS

Communication pursuant to Article 94(3) EPC issued by the European Patent Office on Nov. 18, 2024, which corresponds to European Patent Application No. 23 176 228.7-1122 and is related to U.S. Appl. No. 18/324,602.

(Continued)

*Primary Examiner* — Christopher Koharski
*Assistant Examiner* — Helene Bor
(74) *Attorney, Agent, or Firm* — Studebaker Brackett PLLC

(57) ABSTRACT

There are provided an ultrasound diagnostic apparatus and a control method of the ultrasound diagnostic apparatus which can discriminate an examination site with high accuracy regardless of a skill level of an examiner. An ultrasound diagnostic apparatus includes an image acquisition unit in which an ultrasound image of a subject is input by an examiner performing ultrasonography on the subject; and a site discrimination unit that discriminates an examination site shown in the ultrasound image on the basis of posture information of the examiner and the subject, which is acquired by analyzing reflection signals in a case of transmitting detection signals from a distance measurement device toward the examiner and the subject, and the ultrasound image acquired by the image acquisition unit.

9 Claims, 3 Drawing Sheets

(56) References Cited

U.S. PATENT DOCUMENTS

| | | | | |
|---|---|---|---|---|
| 2010/0087756 | A1* | 4/2010 | Egorov | A61B 5/4312 600/587 |
| 2012/0203106 | A1* | 8/2012 | Matsunaga | A61B 8/06 600/443 |
| 2013/0245428 | A1* | 9/2013 | Banjanin | A61B 8/4263 600/424 |
| 2014/0171799 | A1* | 6/2014 | Hershey | A61B 8/4254 600/440 |
| 2018/0160981 | A1* | 6/2018 | Tsymbalenko | A61B 8/5215 |
| 2018/0225993 | A1* | 8/2018 | Buras | G09B 5/065 |
| 2018/0344289 | A1 | 12/2018 | Mai | |
| 2019/0350561 | A1 | 11/2019 | Ebata | |
| 2021/0045717 | A1* | 2/2021 | Schwab | A61B 5/1128 |
| 2021/0065365 | A1 | 3/2021 | Odagiri | |
| 2021/0065370 | A1 | 3/2021 | Kotoku et al. | |

FOREIGN PATENT DOCUMENTS

| | | | |
|---|---|---|---|
| JP | 2021-29676 | A | 3/2021 |
| WO | 2017/145540 | A1 | 8/2017 |
| WO | 2018/142954 | A1 | 8/2018 |
| WO | 2021/231190 | A1 | 11/2021 |

OTHER PUBLICATIONS

The extended European search report issued by the European Patent Office on Jul. 26, 2023, which corresponds to European Patent Application No. 23176228.7-1126 and is related to U.S. Appl. No. 18/324,602.

Zhao Mingmin et al., “Through-Wall Human Pose Estimation Using Radio Signals”, 2018 IEEE/CVF Conference on Computer Vision and Pattern Recognition, Jun. 18, 2018, pp. 7356-7365, doi: 10.1109/CVPR.2018.00768, IEEE.

Communication pursuant to Article 94(3) EPC issued by the European Patent Office on Jul. 8, 2025, which corresponds to European Patent Application No. 23 176 228.7-1122 and is related to U.S. Appl. No. 18/324,602.

An Office Action, “Notice of Reasons for Refusal,” mailed by the Japanese Patent Office on Nov. 25, 2025, which corresponds to Japanese Patent Application No. 2022-087604 and is related to U.S. Appl. No. 18/324,602; with English language translation.

* cited by examiner

ULTRASOUND DIAGNOSTIC APPARATUS AND CONTROL METHOD OF ULTRASOUND DIAGNOSTIC APPARATUS

CROSS-REFERENCE TO RELATED APPLICATIONS

The present application claims priority under 35 U.S.C. § 119 to Japanese Patent Application No. 2022-087604, filed on May 30, 2022. The above application is hereby expressly incorporated by reference, in its entirety, into the present application.

BACKGROUND OF THE INVENTION

1. Field of the Invention

The present invention relates to an ultrasound diagnostic apparatus, and a control method of the ultrasound diagnostic apparatus which specify an examination position of a subject.

2. Description of the Related Art

In the related art, an ultrasound image representing a tomographic image of an inside of a subject is captured using a so-called ultrasound diagnostic apparatus. Usually, an examiner often discriminates an examination site of the subject, which is currently being imaged, by checking the ultrasound image. However, since the appearance of the ultrasound image varies depending on various factors such as the difference in the shape of the site depending on the subject and the difference in the tomographic plane being scanned, the examiner may erroneously discriminate the examination site only by checking the ultrasound image especially in a case where the skill level of the examiner is low.

In order to prevent such erroneous discrimination of the site, for example, as disclosed in WO2017/145540A and WO2018/142954A, techniques have been developed for automatically discriminating the examination site by analyzing ultrasound images.

SUMMARY OF THE INVENTION

According to the techniques disclosed in WO2017/145540A and WO2018/142954A, the examination site is automatically discriminated regardless of the skill level of the examiner, but for some reason, the analysis of the ultrasound images may not be normally performed, and there is room for improvement in the accuracy of discriminating the examination site.

The present invention has been made in order to solve such a problem in the related art, and an object of the invention is to provide an ultrasound diagnostic apparatus and a control method of the ultrasound diagnostic apparatus which can discriminate an examination site with high accuracy regardless of a skill level of an examiner.

According to the following configuration, the above object can be achieved.

[1] An ultrasound diagnostic apparatus includes an image acquisition unit in which an ultrasound image of a subject is input by an examiner performing ultrasonography on the subject; and a site discrimination unit that discriminates an examination site shown in the ultrasound image on the basis of posture information of the examiner and the subject, which is acquired by analyzing reflection signals in a case of transmitting detection signals from a distance measurement device toward the examiner and the subject, and the ultrasound image acquired by the image acquisition unit.

[2] The ultrasound diagnostic apparatus described in [1], in which the site discrimination unit determines the examination site on the basis of the posture information and the ultrasound image by using a learning model trained for a relationship between postures of the examiner and the subject, the ultrasound image captured in a case where the examiner and the subject are in the postures, and the examination site of the subject.

[3] The ultrasound diagnostic apparatus described in [2], in which the learning model includes a plurality of sub-learning models that correspond to a plurality of predetermined segments of a human body and are trained for the relationship between the ultrasound image and the examination site of the subject, selects one sub-learning model from among the plurality of sub-learning models on the basis of the posture information, and discriminates the examination site in the corresponding segment by the one sub-learning model on the basis of the ultrasound image.

[4] The ultrasound diagnostic apparatus described in [3], in which the learning model has a plurality of candidate sites for the examination site, selects at least one candidate site from among the plurality of candidate sites on the basis of the posture information, and outputs one candidate site of the at least one candidate site as the examination site on the basis of the ultrasound image.

[5] The ultrasound diagnostic apparatus described in any one of [1] to [4], further including an information memory that stores the posture information and the ultrasound image in association with each other.

[6] The ultrasound diagnostic apparatus described in any one of [1] to [5], in which the image acquisition unit includes an ultrasound probe, and an image generation unit that generates the ultrasound image of the subject by performing transmission and reception of ultrasound beams using the ultrasound probe.

[7] A control method of an ultrasound diagnostic apparatus includes acquiring an ultrasound image of a subject; and discriminating an examination site shown in the ultrasound image on the basis of posture information of an examiner and the subject, which is acquired by analyzing reflection signals in a case of transmitting detection signals from a distance measurement device toward the examiner and the subject, and the ultrasound image.

According to the present invention, an ultrasound diagnostic apparatus includes an image acquisition unit in which an ultrasound image of a subject is input by an examiner performing ultrasonography on the subject; and a site discrimination unit that discriminates an examination site shown in the ultrasound image on the basis of posture information of the examiner and the subject, which is acquired by analyzing reflection signals in a case of transmitting detection signals from a distance measurement device toward the examiner and the subject, and the ultrasound image acquired by the image acquisition unit. Therefore, the examination site can be discriminated with high accuracy regardless of the skill level of the examiner.

DESCRIPTION OF THE PREFERRED EMBODIMENTS

Hereinafter, embodiments of the invention will be described with reference to the accompanying drawings.

The description of configuration requirements described below is given on the basis of the representative embodiment of the present invention, but the present invention is not limited to such an embodiment.

In the present specification, a numerical range represented using "to" means a range including the numerical values before and after "to" as a lower limit value and an upper limit value.

In the present specification, the terms "same" and "identical" include an error range generally allowed in the technical field.

Embodiment

Figure 1:
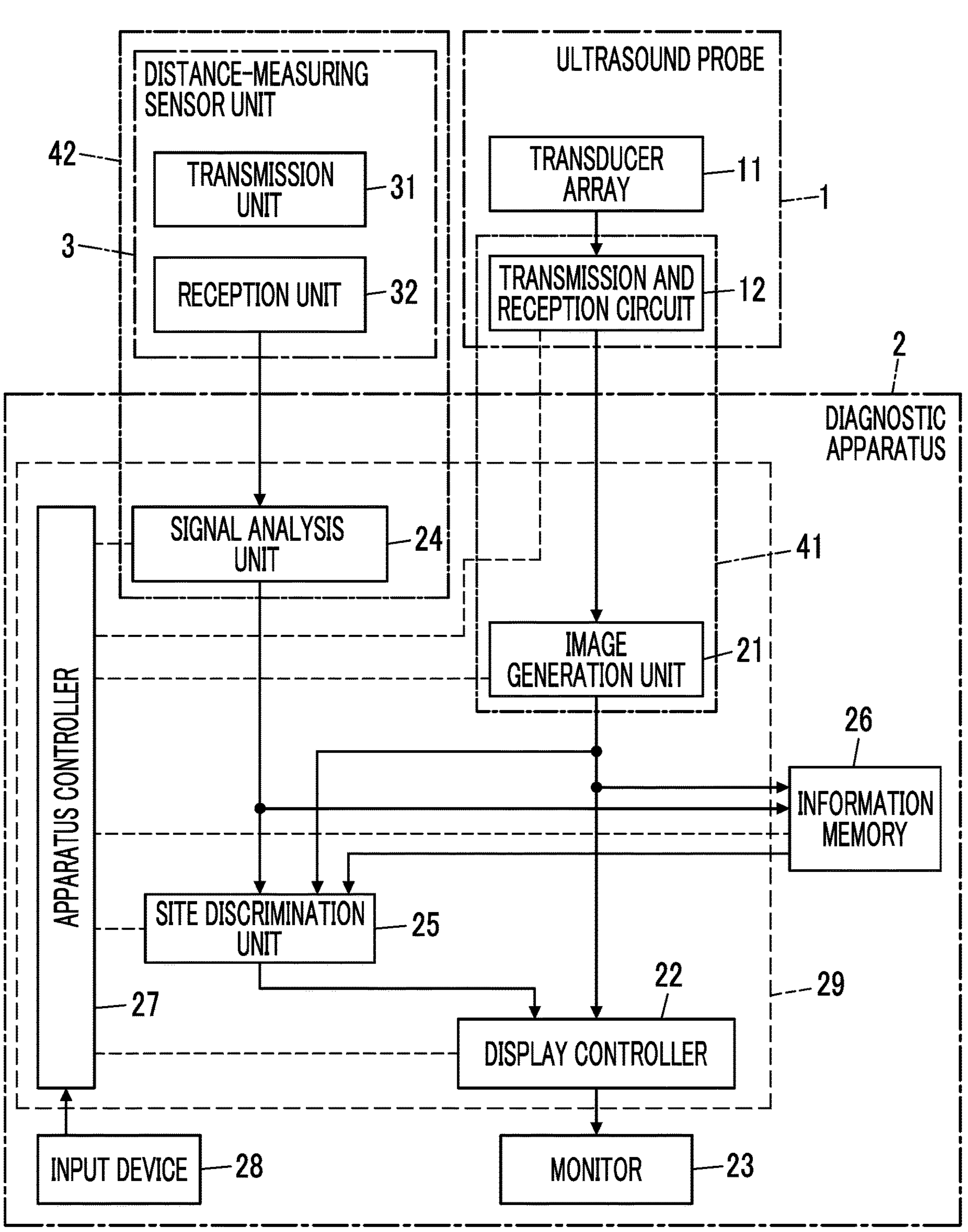
FIG. 1 is a block diagram illustrating a configuration of an ultrasound diagnostic apparatus according to an embodiment of the present invention.

FIG. 1 illustrates a configuration of an ultrasound diagnostic apparatus according to an embodiment of the present invention. The ultrasound diagnostic apparatus includes an ultrasound probe 1, a diagnostic apparatus 2 connected to the ultrasound probe 1, and a distance-measuring sensor unit 3 connected to the diagnostic apparatus 2.

The ultrasound probe 1 includes a transducer array 11, and a transmission and reception circuit 12 is connected to the transducer array 11. Further, the distance-measuring sensor unit 3 includes a transmission unit 31 and a reception unit 32.

The diagnostic apparatus 2 is connected to the ultrasound probe 1, and displays an ultrasound image captured by the ultrasound probe 1. The diagnostic apparatus 2 is used for the examiner to check the ultrasound image captured in real time by the ultrasound probe 1, for example.

The diagnostic apparatus 2 includes an image generation unit 21 connected to the transmission and reception circuit 12 of the ultrasound probe 1, and a display controller 22 and a monitor 23 are sequentially connected to the image generation unit 21. The image generation unit 21 and the ultrasound probe 1 constitute an image acquisition unit 41. The diagnostic apparatus 2 includes a signal analysis unit 24 connected to the reception unit 32 of the distance-measuring sensor unit 3. A site discrimination unit 25 is connected to the image generation unit 21 and the signal analysis unit 24. The site discrimination unit 25 is connected to the display controller 22. The image generation unit 21 and the signal analysis unit 24 are connected to an information memory 26. An apparatus controller 27 is connected to the transmission and reception circuit 12, the display controller 22, the signal analysis unit 24, the site discrimination unit 25, and the information memory 26. An input device 28 is connected to the apparatus controller 27.

The image generation unit 21, the display controller 22, the signal analysis unit 24, the site discrimination unit 25, and the apparatus controller 27 constitute a processor 29 for the diagnostic apparatus 2. The signal analysis unit 24 of the diagnostic apparatus 2 and the distance-measuring sensor unit 3 constitute a distance measurement device 42.

The transducer array 11 of the ultrasound probe 1 has a plurality of ultrasonic transducers arranged in a one-dimensional or two-dimensional manner. According to a drive signal supplied from the transmission and reception circuit 12, each of the ultrasonic transducers transmits an ultrasonic wave and receives an ultrasound echo from the subject to output a signal based on the ultrasound echo. For example, each ultrasonic transducer is configured by forming electrodes at both ends of a piezoelectric body consisting of piezoelectric ceramic represented by lead zirconate titanate (PZT), a polymer piezoelectric element represented by poly vinylidene di fluoride (PVDF), piezoelectric single crystal represented by lead magnesium niobate-lead titanate (PMN-PT), or the like.

Figure 2:
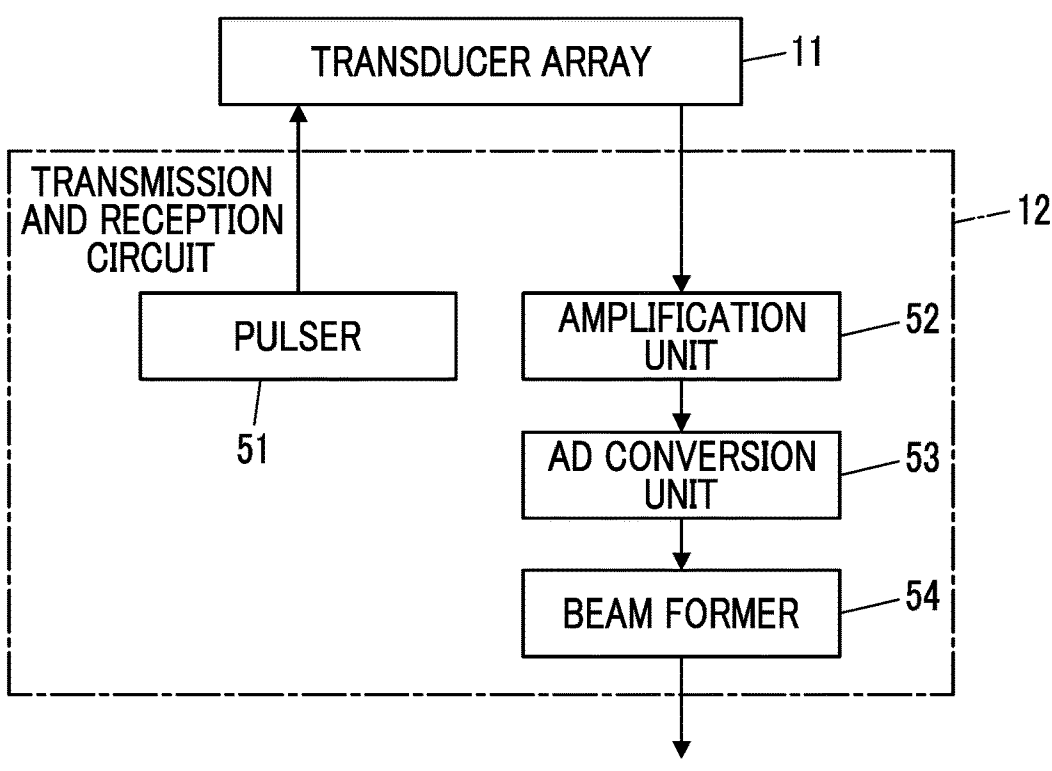
FIG. 2 is a block diagram illustrating a configuration of a transmission and reception circuit in the embodiment of the present invention.

The transmission and reception circuit 12 causes the transducer array 11 to transmit the ultrasonic wave and generates a sound ray signal on the basis of a reception signal acquired by the transducer array 11, under the control of the apparatus controller 27. As illustrated in FIG. 2, the transmission and reception circuit 12 has a pulser 51 connected to the transducer array 11, and an amplification unit 52, an analog to digital (AD) conversion unit 53, and a beam former 54 that are sequentially connected in series from the transducer array 11.

The pulser 51 includes, for example, a plurality of pulse generators, and the pulser 51 adjusts the amount of delay of each drive signal so that ultrasonic waves transmitted from the plurality of ultrasonic transducers of the transducer array 11 form an ultrasound beam on the basis of a transmission delay pattern selected according to the control signal from the apparatus controller 27, and supplies the obtained signals to the plurality of ultrasonic transducers. Thus, in a case where a pulsed or continuous-wave voltage is applied to the electrodes of the ultrasonic transducers of the transducer array 11, the piezoelectric body expands and contracts to generate pulsed or continuous-wave ultrasonic waves from each ultrasonic transducer. From the combined wave of these ultrasonic waves, an ultrasound beam is formed.

The transmitted ultrasound beam is reflected by a target, for example, a site of the subject, and propagates toward the transducer array 11 of the ultrasound probe 1. The ultrasound echo propagating toward the transducer array 11 in this manner is received by each ultrasonic transducer constituting the transducer array 11. In this case, each ultrasonic transducer constituting the transducer array 11 expands and contracts by receiving the propagating ultrasound echo to generate a reception signal that is an electric signal, and outputs the reception signal to the amplification unit 52.

The amplification unit 52 amplifies the signals input from each ultrasonic transducer constituting the transducer array 11, and transmits the amplified signals to the AD conversion unit 53. The AD conversion unit 53 converts the signal transmitted from the amplification unit 52 into digital reception data. The beam former 54 performs so-called reception focusing processing in which addition is performed by giving delays to respective pieces of the reception data received from the AD conversion unit 53. Through the reception focusing processing, a sound ray signal in which each piece of the reception data converted by the AD conversion unit 53 is phased and added and the focus of the ultrasound echo is narrowed is acquired.

Figure 3:
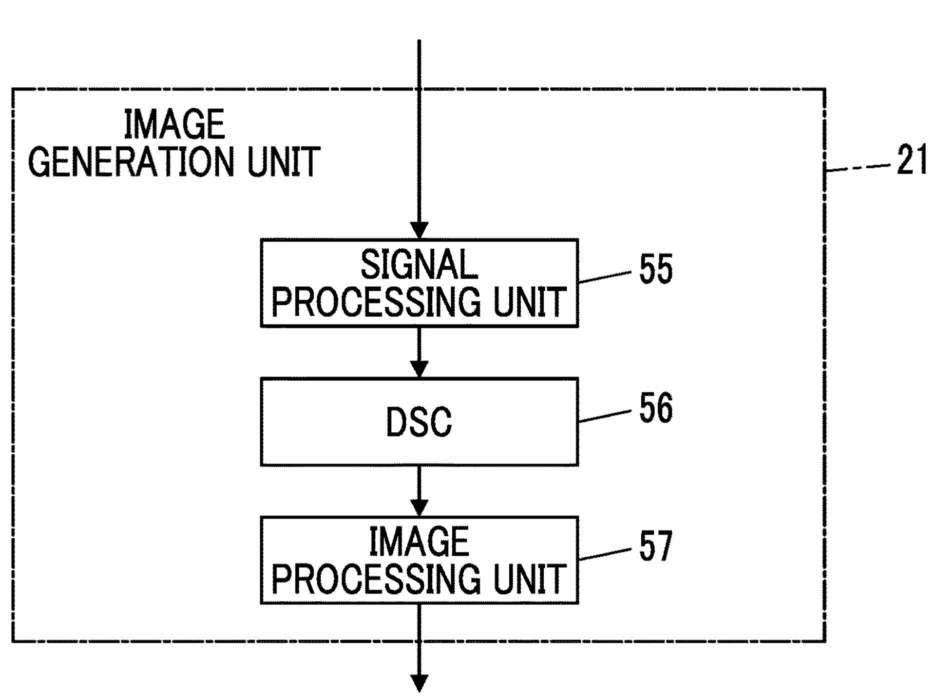
FIG. 3 is a block diagram illustrating a configuration of an image generation unit in the embodiment of the present invention.

As illustrated in FIG. 3, the image generation unit 21 has a configuration in which a signal processing unit 55, a digital scan converter (DSC) 56, and an image processing unit 57 are sequentially connected in series.

The signal processing unit 55 generates a B-mode image signal, which is tomographic image information regarding tissues inside the subject, by performing, on the sound ray signal received from the transmission and reception circuit 12, correction of the attenuation due to the distance according to the depth of the reflection position of the ultrasonic wave using a sound speed value set by the apparatus controller 27 and then performing envelope detection processing.

The DSC 56 converts (raster conversion) the B-mode image signal generated by the signal processing unit 55 into an image signal according to a normal television signal scanning method.

The image processing unit 57 performs various kinds of necessary image processing such as gradation processing on the B-mode image signal input from the DSC 56, and then sends the B-mode image signal to the display controller 22, the site discrimination unit 25, and the information memory 26. In this manner, the B-mode image signal subjected to the image processing by the image processing unit 57 is simply referred to as an ultrasound image.

The display controller 22 performs predetermined processing on the ultrasound image or the like generated by the image generation unit 21 and displays the ultrasound image or the like on the monitor 23, under the control of the apparatus controller 27.

The monitor 23 performs various kinds of display under the control of the apparatus controller 27. The monitor 23 can include a display device such as a liquid crystal display (LCD), or an organic electroluminescence (EL) display.

Figure 4:
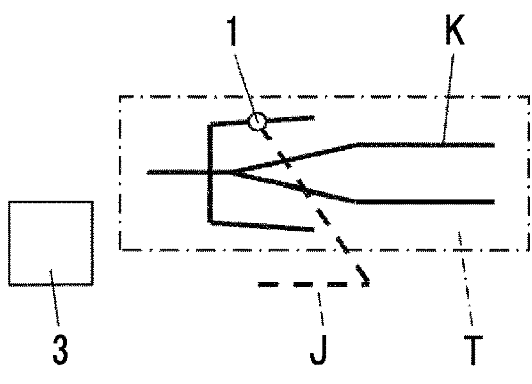
FIG. 4 is a diagram schematically illustrating an example of a positional relationship between a distance-measuring sensor unit, a subject, and an examiner in the embodiment of the present invention.

For example, as illustrated in FIG. 4, the distance-measuring sensor unit 3 is arranged near a subject K and an examiner J who performs an examination for the subject K by using the ultrasound probe 1, transmits detection signals toward the examiner J and the subject K, and receives reflection signals reflected from the examiner and the subject. The example of FIG. 4 illustrates an aspect in which the subject K is lying on an examination table T, and the examiner J examines the arm of the subject K with the ultrasound probe 1.

The transmission unit 31 of the distance-measuring sensor unit 3 transmits detection signals toward the examiner J and the subject K. The transmission unit 31 is a so-called radio transmitter for electromagnetic waves, and includes, for example, an antenna for transmitting electromagnetic waves, a signal source such as an oscillation circuit, a modulation circuit for modulating signals, an amplifier for amplifying signals, and the like.

The reception unit 32 includes an antenna or the like for receiving electromagnetic waves, and receives reflection signals from the examiner J and the subject K.

The distance-measuring sensor unit 3 can include, for example, a radar that transmits and receives a so-called Wi-Fi (registered trademark) standard detection signals consisting of electromagnetic waves having a center frequency of 2.4 GHz or 5 GHz, and can also include a radar that transmits and receives wideband detection signals having a center frequency of 1.78 GHz. In addition, the distance-measuring sensor unit 3 can also include a so-called light detection and ranging or laser imaging detection and ranging (LIDAR) sensor that transmits short-wavelength electromagnetic waves such as ultraviolet rays, visible rays, or infrared rays as detection signals.

The signal analysis unit 24 of the diagnostic apparatus 2 acquires posture information of the examiner J and the subject K by analyzing the reflection signals received by the distance-measuring sensor unit 3. The posture information of the examiner J and the subject K includes information regarding the position of each site of the examiner J and the subject K, such as the heads, shoulders, arms, waists, and legs of the examiner J and the subject K, for example.

The signal analysis unit 24 can acquire the posture information of the examiner J and the subject K by using a machine learning model trained for the reflection signals in a case where the distance-measuring sensor unit 3 transmits the detection signals toward the human body. Specifically, the signal analysis unit 24 can acquire the posture information by using, for example, a method described in "ZHAO, Mingmin, et al. Through-wall human pose estimation using radio signals. In: Proceedings of the IEEE Conference on Computer Vision and Pattern Recognition. 2018. p. 7356-7365.", "VASILEIADIS, Manolis; BOUGANIS, Christos-Savvas; TZOVARAS, Dimitrios. Multi-person 3D pose estimation from 3D cloud data using 3D convolutional neural networks. Computer Vision and Image Understanding, 2019, 185: 12-23.", "JIANG, Wenjun, et al. Towards 3D human pose construction using WiFi. In: Proceedings of the 26th Annual International Conference on Mobile Computing and Networking. 2020. p. 1-14.", or "WANG Fei, et al. Person-in-WiFi: Fine-grained person perception using WiFi. In: Proceedings of the IEEE/CVF International Conference on Computer Vision. 2019. p. 5452-5461.".

The signal analysis unit 24 can set a coordinate system using a position of one site of the subject K as the origin, and acquire three-dimensional coordinates of the position of each site of the subject K as the posture information of the subject K. For example, the signal analysis unit 24 can set the three-dimensional coordinate system by setting the position of the neck of the subject K as the origin of the coordinate system, an axis along a straight line passing through the left and right shoulders of the subject as a first axis, an axis along a straight line orthogonal to the first axis and passing through the head and the torso of the subject K as a second axis, and an axis orthogonal to both the first axis and the second axis as a third axis. As a result, for example, even in a case where the positional relationship between the distance-measuring sensor unit 3 and the subject K differs for each examination, the position of each site of the subject K can be expressed in the same three-dimensional coordinate system.

Here, the position on the subject K where the tip of the arm of the examiner J is positioned can be specified as the position on the subject K with which the ultrasound probe 1 is in contact by the examiner J. Therefore, in a case where the human body is divided into a plurality of segments, the segment on the subject K where the examination is currently being performed can be specified on the basis of the posture information of the subject K and the examiner J.

Further, for example, the site of the subject K shown in the ultrasound image can be discriminated by using so-called machine learning or deep learning that has learned the relationship between the features of the tissue structure shown in the ultrasound image and the name of the site of the subject K corresponding to the tissue structure or an image analysis and the like such as template matching. However, for some reasons such as that the shape and size of the anatomical structure differ depending on the subject, or that a clear ultrasound image cannot be obtained due to the low skill level of the examiner J, in a case of trying to discriminate the examination site only on the basis of the ultrasound image, the examination site may be erroneously discriminated.

Thus, in order to improve the accuracy of discriminating the examination site, the site discrimination unit 25 discriminates the examination site shown in the ultrasound image on the basis of both the posture information of the subject K and the examiner J acquired by the signal analysis unit 24 and the ultrasound image of the subject K generated by the image generation unit 21. As a result, since the segmentation of the body of the subject K specified from the posture information of the subject K and the examiner J is taken into account in a case of discriminating the examination site based on the ultrasound image, the examination site can be discriminated with high accuracy.

In this case, for example, the site discrimination unit 25 can discriminate the current examination site of the subject on the basis of the posture information of the subject K and the examiner J acquired by the signal analysis unit 24 and the ultrasound image generated by the image generation unit 21 by using a learning model trained for the relationship between the postures of the subject K and the examiner J, the ultrasound image captured in a case where the subject K and the examiner J are in the postures, and the examination site of the subject.

More specifically, a learning model of the site discrimination unit 25 has a plurality of predetermined candidate sites as candidates for the examination site, and can calculate a probability that the examination site shown in the ultrasound image is each of the plurality of candidate sites. In this case, the learning model can weight the probability of at least one candidate site corresponding to the segment of the body of the subject specified from the posture information of the subject K and the examiner J, for example. The learning model can discriminate the candidate site corresponding to the maximum probability among the calculated probabilities of the plurality of candidate sites, as the examination site.

The site discrimination unit 25 can use, as the learning model, for example, a model in accordance with an algorithm such as so-called residual neural network (ResNet), dense convolutional network (DenseNet), AlexNet, Baseline, batch normalization, Dropout regularization, NetWidth search, or NetDepth search. In addition, the site discrimination unit 25 can also use models in accordance with these algorithms in combination as appropriate.

In this manner, the site discrimination unit 25 determines the current examination site by using not only the ultrasound image of the subject K but also the posture information of the subject K and the examiner J supplementally. Therefore, regardless of the skill level of the examiner J, the examination site can be discriminated with high accuracy. Furthermore, for example, the examination site can be determined more accurately than a case where the examination site is determined only on the basis of the ultrasound image.

The learning model of the site discrimination unit 25 includes a plurality of sub-learning models that correspond to a plurality of predetermined segments of the human body and are trained for the relationship between the ultrasound image and the examination site of the subject K. In this case, the learning model can select one sub-learning model corresponding to the segment of the body of the subject K specified from the posture information, from among the plurality of sub-learning models, and discriminate the examination site in the corresponding segment by inputting the ultrasound image to the selected sub-learning model. More specifically, for example, the learning model includes sub-learning models for the abdomen, the chest, the upper limb, and the like, and discriminates one of the candidate sites such as a liver and a kidney positioned in the abdomen as the examination site in a case where the segment of the body specified from the posture information of the subject K and the examiner J is the abdomen.

The learning model can include one learning model, select at least one candidate site included in the segment of the human body specified on the basis of the posture information of the subject K and the examiner J from among the plurality of candidate sites, and output one candidate site among the at least one selected candidate site, as the examination site on the basis of the ultrasound image. For example, the learning model has a liver, a kidney, a heart, a lung, and a thoracic diaphragm as the plurality of predetermined candidate sites, and can select a liver and a kidney corresponding to the abdomen as the candidate site from among the plurality of candidate sites in a case where the abdomen of the subject K is specified from the posture information of the subject K and the examiner J. In this case, the learning model calculates a probability that the liver is the examination site and a probability that the kidney is the examination site, and discriminates a site having the maximum probability among the probabilities as the examination site. In this case, for example, since the processing of calculating the probability is performed on at least one candidate site among the plurality of candidate sites, the calculation load in the site discrimination unit 25 can be reduced.

The learning model can calculate each probability for each of the plurality of candidate sites on the basis of the ultrasound image, and then select at least one candidate site from among the plurality of candidate sites on the basis of the posture information of the subject K and the examiner J. For example, the learning model has a liver, a kidney, a heart, a lung, and a thoracic diaphragm as the plurality of predetermined candidate sites, and can select a liver and a kidney as the candidate site from among the liver, the kidney, the heart, the lung, and the thoracic diaphragm for which the probability is calculated, in a case where the abdomen of the subject K is specified from the posture information of the subject K and the examiner J. In this case, the learning model discriminates a site having the maximum probability among a probability that the liver is the examination site and a probability that the kidney is the examination site, as the examination site. For example, even in a case where the probability corresponding to the heart, the lung, or the thoracic diaphragm becomes greater than the probability corresponding to the liver and the kidney due to some reasons, since the liver and the kidney are selected as the candidate site on the basis of the posture information, the examination site can be accurately discriminated.

In addition, the site discrimination unit 25 can discriminate the examination site without using the learning model. For example, the site discrimination unit 25 can have template data representing a typical shape or the like of each of the plurality of candidate sites, calculate the probability that the examination site is each of the plurality of candidate sites by a so-called template matching method of comparing the anatomical structure shown in the ultrasound image with the plurality of pieces of template data, and discriminate the examination site on the basis of the calculated probability.

In this case, the site discrimination unit 25 can weight the probability of at least one site corresponding to the segment of the body specified from the posture information of the subject K and the examiner J. The site discrimination unit 25 can discriminate the examination site after selecting at least one site corresponding to the segment of the body specified from the posture information of the subject K and the examiner J from among the plurality of predetermined candidate sites.

The site discrimination unit 25 can display the name and the like of the discriminated examination site of the subject on the monitor 23.

The information memory 26 stores both the posture information of the subject K and the examiner J acquired by the signal analysis unit 24 and the ultrasound image generated by the image generation unit 21 corresponding to the posture information in association with each other, under the control of the apparatus controller 27. For example, the information memory 26 can associate the posture information with the ultrasound image by describing the examination position in so-called header information of the ultrasound image, under the control of the apparatus controller 27. The information memory 26 can associate the posture information with the ultrasound image by, for example, a so-called time stamp or so-called Digital Imaging and Communications in Medicine (DICOM), under the control of the apparatus controller 27. The ultrasound image and the posture information of the subject K and the examiner J stored in the information memory 26 can be read by an input operation by the examiner J or the like via the input device 28 and sent to the site discrimination unit 25, for example. As a result, for example, even after the examination is ended, the site discrimination unit 25 can determine the examination site shown in the ultrasound image with high accuracy regardless of the skill level of the examiner J.

Here, as the information memory 26, for example, recording media such as a flash memory, a hard disk drive (HDD), a solid state drive (SSD), a flexible disk (FD), a magneto-optical disk (MO disk), a magnetic tape (MT), a random access memory (RAM), a compact disc (CD), a digital versatile disc (DVD), a secure digital card (SD card), or a universal serial bus memory (USB memory) can be used.

The apparatus controller 27 controls each unit of the diagnostic apparatus 2 according to a program and the like stored in advance.

The input device 28 accepts the input operation by the examiner J or the like, and sends the input information to the apparatus controller 27. The input device 28 is configured by, for example, a device for the examiner to perform an input operation, such as a keyboard, a mouse, a trackball, a touchpad, a touch panel, or the like.

The processor 29 having the image generation unit 21, the display controller 22, the signal analysis unit 24, the site discrimination unit 25, and the apparatus controller 27 of the diagnostic apparatus 2 is configured by a central processing unit (CPU) and a control program for causing the CPU to execute various kinds of processing, but the processor 29 may be configured by using a field programmable gate array (FPGA), a digital signal processor (DSP), an application specific integrated circuit (ASIC), a graphics processing unit (GPU), or other integrated circuits (IC) or may be configured by a combination thereof.

In addition, the image generation unit 21, the display controller 22, the signal analysis unit 24, the site discrimination unit 25, and the apparatus controller 27 of the processor 29 can also be configured by being integrated partially or entirely into one CPU or the like.

Next, an example of the operation of the ultrasound diagnostic apparatus according to the embodiment will be described using the flowchart illustrated in FIG. 5.

First, in Step S1, the distance-measuring sensor unit 3 starts to continuously transmit detection signals toward the subject K and the examiner J and to continuously receive reflection signals from the subject K and the examiner J. In this case, the examiner J brings the ultrasound probe 1 into contact with the body surface of the subject K.

Next, in Step S2, the signal analysis unit 24 detects the subject K and the examiner J by analyzing the reflection signals received by the distance-measuring sensor unit 3 in Step S1.

Subsequently, in Step S3, the signal analysis unit 24 acquires the posture information of the subject K and the examiner J detected in Step S2 by analyzing the reflection signals received by the distance-measuring sensor unit 3 in Step S1. In this case, the signal analysis unit 24 can set a coordinate system using one site of the subject K as the origin, and acquire three-dimensional coordinates of the position of each site of the subject K as the posture information of the subject K. For example, the signal analysis unit 24 can set the three-dimensional coordinate system by setting the position of the neck of the subject K as the origin of the coordinate system, an axis along a straight line passing through the left and right shoulders of the subject as a first axis, an axis along a straight line orthogonal to the first axis and passing through the head and the torso of the subject K as a second axis, and an axis orthogonal to both the first axis and the second axis as a third axis. As a result, for example, even in a case where the positional relationship between the distance-measuring sensor unit 3 and the subject K differs for each examination, the position of each site of the subject K can be expressed in the same three-dimensional coordinate system.

The posture information of the subject K and the examiner J acquired in Step S3 in this manner is sent to the site discrimination unit 25 and the information memory 26.

In Step S4, the inside of the subject K is scanned by the ultrasound probe 1 while the ultrasound probe 1 is in contact with the body surface of the subject K, and the ultrasound image representing the tomographic image in the subject K is acquired. In this case, the transmission and reception circuit 12 performs so-called reception focusing processing under the control of the apparatus controller 27 to generate sound ray signals. The sound ray signals generated by the transmission and reception circuit 12 are sent to the image generation unit 21. The image generation unit 21 generates the ultrasound image using the sound ray signals sent from the transmission and reception circuit 12. The ultrasound image acquired in this manner is sent to the site discrimination unit 25 and the information memory 26.

Here, the posture information of the subject K and the examiner J sent to the information memory 26 in Step S3 and the ultrasound image sent to the information memory 26 in Step S4 can be stored in the information memory 26 in association with each other, under the control of the apparatus controller 27.

In Step S5, the site discrimination unit 25 discriminates the examination site shown in the ultrasound image on the basis of both the posture information of the subject K and the examiner J acquired in Step S3 and the ultrasound image generated by the image generation unit 21 in Step S4. For example, the site discrimination unit 25 can have a learning model trained in advance for the relationship between the posture of the subject K and the examiner, the ultrasound image acquired corresponding to the posture, and the examination site shown in the ultrasound image, and discriminate the examination site by inputting the posture information of the subject K and the examiner J and the ultrasound image to the learning model.

Here, the segment of the body of the subject K for the ultrasound image is captured can be specified by the posture information of the subject K and the examiner J. Therefore, for example, by taking the specified segmentation of the body of the subject K into account in a case of discriminating the examination site on the basis of the ultrasound image, the accuracy of discriminating the examination site can be improved.

The site discrimination unit 25 displays the information on the examination site discriminated in this manner on the monitor 23. The examiner J can proceed the examination for the subject while easily understanding the current examination site by checking the information on the examination site displayed on the monitor 23.

In Step S6, the apparatus controller 27 determines whether or not to end the examination. For example, in a case where instruction information to end the examination is input by the examiner J via the input device 28, the apparatus controller 27 can determine to end the current examination. Further, for example, in a case where instruction information to end the examination is not input by the examiner J via the input device 28, it is determined the current examination is continued.

In a case where it is determined in Step S6 that the examination is continued, the processing returns to Step S3. As described above, the processing of Step S3 to Step S6 is repeated as long as it is determined in Step S6 that the examination is continued.

Figure 5:
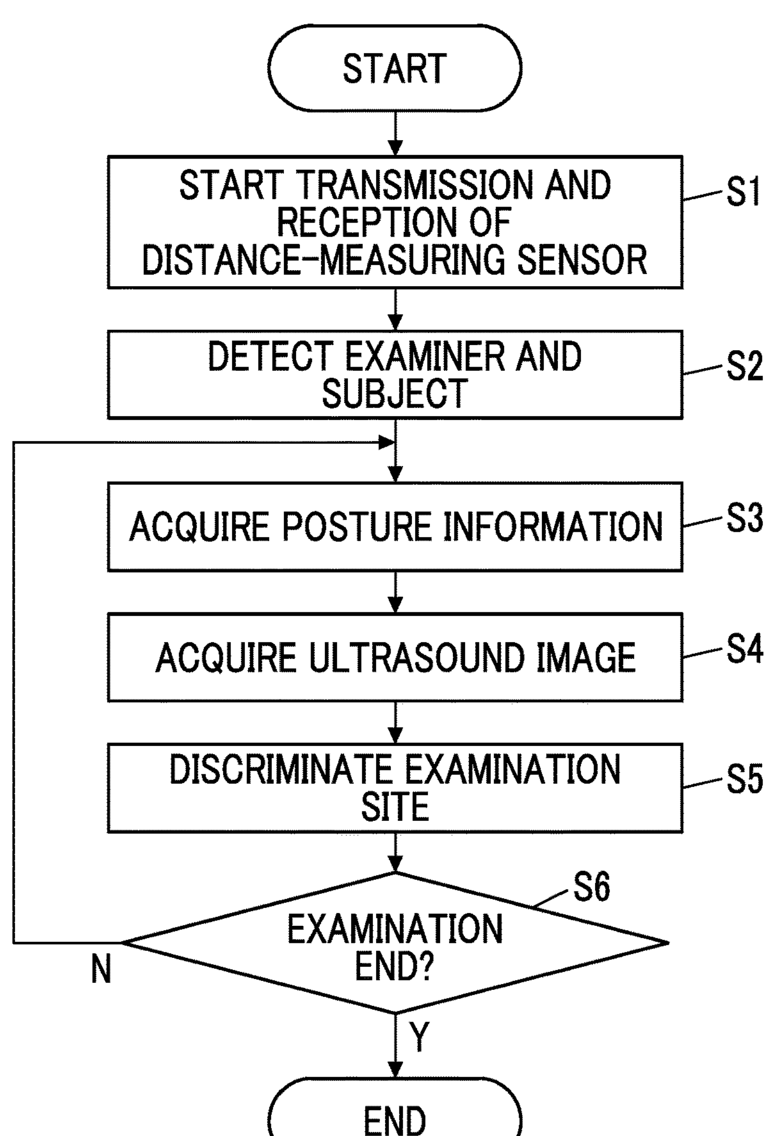
FIG. 5 is a flowchart illustrating an operation of the ultrasound diagnostic apparatus according to the embodiment of the present invention.

In a case where it is determined to end the examination in Step S6, each unit of the ultrasound diagnostic apparatus is controlled so as to end the examination by the apparatus controller 27, and the operation of the ultrasound diagnostic apparatus according to the flowchart of FIG. 5 is ended.

Here, after the examination is ended, for example, the posture information and the ultrasound image stored in association with each other can be read from the information memory 26 on the basis of the input operation by the examiner J or the like via the input device 28. In this case, the site discrimination unit 25 can discriminate the examination site shown in the read ultrasound image on the basis of the posture information of the subject K and the examiner J and the ultrasound image read from the information memory 26. As a result, for example, in a case where a doctor or the like performs a diagnosis for the subject by checking the ultrasound image, the doctor or the like can accurately understand the examination site shown in the ultrasound image by checking the name of the examination site discriminated by the site discrimination unit 25, and therefore, the accuracy of the diagnosis can be improved.

As described above, with the ultrasound diagnostic apparatus according to the embodiment of the present invention, since the site discrimination unit 25 discriminates the examination site of the subject on the basis of both the posture information of the subject K and the examiner J acquired by the signal analysis unit 24 and the ultrasound image generated by the image generation unit 21, the examination site can be discriminated with high accuracy regardless of the skill level of the examiner J. Furthermore, with the ultrasound diagno stic apparatus of the embodiment of the present invention, it is possible to improve the accuracy of discriminating the examination site as compared with a case where the examination site is determined on the basis of only the ultrasound image.

It has been described that the signal analysis unit 24 is included in the diagnostic apparatus 2, but the distance-measuring sensor unit 3 and the signal analysis unit 24 can constitute the distance measurement device 42 separate from the diagnostic apparatus 2, for example. In this case, the posture information of the subject K and the examiner J is acquired by the signal analysis unit 24 of the distance measurement device 42, and the acquired posture information is sent to the site discrimination unit 25 of the diagnostic apparatus 2. Therefore, even in this case, similar to the case where the diagnostic apparatus 2 includes the signal analysis unit 24, the site discrimination unit 25 discriminates the examination site on the basis of both the posture information of the subject K and the examiner J acquired by the signal analysis unit 24 and the ultrasound image generated by the image generation unit 21.

Further, for example, FIG. 2 illustrates that the distance-measuring sensor unit 3 is installed near the examiner J and the subject K, but the installation position of the distance-measuring sensor unit 3 is not particularly limited as long as the detection signals transmitted from the distance-measuring sensor unit 3 reach the examiner J and the subject K. For example, the distance-measuring sensor unit 3 can be installed on the ceiling of the room where the examiner J performs an examination for the subject K.

It has been described that the signal analysis unit 24 sets the coordinate system using the position of one site of the subject K as the origin, but instead of the signal analysis unit 24, the site discrimination unit 25 can set the coordinate system using the position of one site of the subject K as the origin. In this case, for example, the signal analysis unit 24 can acquire three-dimensional coordinates of each site of the subject K with any position in the room or the like where the distance-measuring sensor unit 3 is installed, as the origin on the basis of the reflection signals transmitted from the reception unit 32 of the distance-measuring sensor unit 3. The site discrimination unit 25 converts the three-dimensional coordinates of each site of the subject K acquired by the signal analysis unit 24 into representation in the three-dimensional coordinate system using the position of one site of the subject K as the origin. Even in such a case, for example, even in a case where the positional relationship between the distance-measuring sensor unit 3 and the subject K differs for each examination, the position of each site of the subject K can be expressed in the same three-dimensional coordinate system.

In the flowchart of FIG. 5, the processing proceeds in the order of Step S3 and Step S4, but Step S3 and Step S4 can be processed in parallel.

In the flowchart of FIG. 5, it has been described that the ultrasound image is generated in Step S4 each time the posture information is acquired in Step S3, but the posture information can be acquired once in Step S3 each time ultrasound images of a plurality of constant frames are generated in Step S4, for example. Further, the ultrasound image of one frame can be generated in Step S4 each time the posture information is acquired a plurality of times in Step S3.

It has been described that the image generation unit 21 is included in the diagnostic apparatus 2, but the image generation unit 21 can be included in the ultrasound probe 1 instead of being included in the diagnostic apparatus 2.

The diagnostic apparatus 2 may be a so-called stationary type, a portable type, or a handheld type configured by a so-called smartphone or tablet computer. As described above, the type of equipment constituting the diagnostic apparatus 2 is not particularly limited.

Further, the ultrasound probe 1 and the diagnostic apparatus 2 can be connected to each other in a wired manner, or can be connected to each other in a wireless manner.

EXPLANATION OF REFERENCES

1: ultrasound probe
2: diagnostic apparatus

3: distance-measuring sensor unit
11: transducer array
12: transmission and reception circuit
21: image generation unit
22: display controller
23: monitor
24: signal analysis unit
25: site discrimination unit
26: information memory
27: apparatus controller
28: input device
29: processor
31: transmission unit
32: reception unit
41: image acquisition unit
42: distance measurement device
51: pulser
52: amplification unit
53: AD conversion unit
54: beam former
55: signal processing unit
56: DSC
57: image processing unit
J: examiner
K: subject
T: examination table

What is claimed is:

1. An ultrasound diagnostic apparatus comprising:

a processor configured to receive an input of an ultrasound image of a subject by an examiner performing ultrasonography on the subject;

transmit signals from a distance measurement device toward the examiner and the subject;

analyze, at the distance measurement device, signals reflected from the examiner and the subject to acquire posture information of the examiner and the subject; and discriminate an examination site shown in the ultrasound image based on the ultrasound image of the subject captured in a posture state indicated by the posture information, and the posture information of each of the examiner and the subject, wherein the processor is configured to discriminate the examination site with a learning model trained for a relationship between postures of each of the examiner and the subject, the ultrasound image of the subject, and the examination site of the subject, the learning model includes a plurality of sub-learning models that correspond to a plurality of predetermined segments of a human body and are trained for the relationship between the ultrasound image captured in the posture state and the examination site of the subject, the learning model selects one sub-learning model from among the plurality of sub-learning models based on the posture information, and the learning model discriminates the examination site in the corresponding segment by the one sub-learning model based on the ultrasound image.

2. The ultrasound diagnostic apparatus according to claim 1, wherein the learning model has a plurality of candidate sites for the examination site, selects at least one candidate site from among the plurality of candidate sites based on the posture information, and outputs the at least one candidate site as the examination site based on the ultrasound image.

3. The ultrasound diagnostic apparatus according to claim 2, further comprising:

an information memory configured to store the posture information and the ultrasound image in association with each other.

4. The ultrasound diagnostic apparatus according to claim 2, further comprising:

an ultrasound probe, and wherein the processor is further configured to generate the ultrasound image of the subject by performing transmission and reception of ultrasound beams using the ultrasound probe.

5. The ultrasound diagnostic apparatus according to claim 1, further comprising:

an information memory configured to store the posture information and the ultrasound image in association with each other.

6. The ultrasound diagnostic apparatus according to claim 1, further comprising:

an information memory configured to store the posture information and the ultrasound image in association with each other.

7. The ultrasound diagnostic apparatus according to claim 1, further comprising:

an ultrasound probe, and wherein the processor is further configured to generate the ultrasound image of the subject by performing transmission and reception of ultrasound beams using the ultrasound probe.

8. The ultrasound diagnostic apparatus according to claim 1, further comprising:

an ultrasound probe, and wherein the processor is further configured to generate the ultrasound image of the subject by performing transmission and reception of ultrasound beams using the ultrasound probe.

9. A control method of an ultrasound diagnostic apparatus, the control method comprising:

transmitting signals from a distance measurement device toward an examiner and a subject;

analyzing, at the distance measurement device, signals reflected from the examiner and the subject to acquire posture information of the examiner and the subject;

acquiring an ultrasound image of the subject; and discriminating, by a processor, an examination site shown in the ultrasound image based on the ultrasound image of the subject captured in a posture state indicated by the posture information, and the posture information of each of the examiner and the subject, wherein the processor is configured to discriminate the examination site with a learning model trained for a relationship between postures of each of the examiner and the subject, the ultrasound image of the subject, and the examination site of the subject, the learning model includes a plurality of sub-learning models that correspond to a plurality of predetermined segments of a human body and are trained for the relationship between the ultrasound image captured in the posture state and the examination site of the subject, the learning model selects one sub-learning model from among the plurality of sub-learning models based on the posture information, and the learning model discriminates the examination site in the corresponding segment by the one sub-learning model based on the ultrasound image.

* * * * *